US008609587B2

(12) United States Patent
Mann et al.

(10) Patent No.: US 8,609,587 B2
(45) Date of Patent: Dec. 17, 2013

(54) SYNERGISTIC HERBICIDAL COMPOSITIONS CONTAINING PROPYZAMIDE AND AMINOPYRALID

(75) Inventors: Richard K. Mann, Franklin, IN (US); Xavier de Gaujac, Peymeinade (FR)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/161,925

(22) Filed: Jun. 16, 2011

(65) Prior Publication Data

US 2011/0312494 A1    Dec. 22, 2011

Related U.S. Application Data

(60) Provisional application No. 61/355,167, filed on Jun. 16, 2010.

(51) Int. Cl.
  *A01N 25/32*  (2006.01)
  *A01N 43/40*  (2006.01)
  *A01N 25/26*  (2006.01)
  *A01N 37/18*  (2006.01)

(52) U.S. Cl.
  USPC ........... 504/112; 504/100; 504/111; 504/130; 504/149

(58) Field of Classification Search
  USPC ......... 504/130, 103, 111, 118, 148, 100, 112, 504/149; 514/277, 354, 487, 741
  See application file for complete search history.

(56) References Cited

FOREIGN PATENT DOCUMENTS

WO  WO 2009/153247 A2  12/2009
WO  WO/2011/159879  12/2011

OTHER PUBLICATIONS

Jewell, S.N., Herbicide Programmes for Broadleaved Weed Control in Winter Oilseed Rape on Organic Soils. Abstract[online]. CABI Databases, 1990 [retrieved on [Jul. 16, 2012]. Retrieved from the Internet: <http://www.cabdirect.org/abstracts/19902301728.html;jsessionid=1452B150B278E0E2C5BE2402DACAEF95#> 1 page.*
Make the Most of Residual-Acting Propyzamide. [online]. FarmingUK, 2007 [retrieved on Apr. 12, 2013]. Retrieved from the Internet<URL:http://www.farminguk.com/News/Make-the-most-of-residual-acting-propyzamide_4304.html, 3 pages.*
Sinclair C et al: "The addition of 3,6-dichloropicolinic acid to propyzamide in winter oilseed rape for control of *Matricaria matricarioides, M. recutita* and *Tripleurospermum maritimum* ssp. inodorum", Conference Info: Proceedings—British Crop Protection Conference—Weeds, vol. 15, No. 2, Jan. 1, 1980, pp. 557-564.
Bekir Bukun et al: "Aminopyralid and Clopyralid Absorption and Translocation in Canada Thistle (*Cirsium arvense*)", Weed Science, Weed Science Society of America, Champaign, IL, US, vol. 57, Jan. 1, 2009, pp. 10-15.

* cited by examiner

*Primary Examiner* — Sue Liu
*Assistant Examiner* — Andriae M Holt
(74) *Attorney, Agent, or Firm* — Robert Chang; Jones Day

(57) ABSTRACT

An herbicidal composition containing (a) propyzamide and (b) aminopyralid provides synergistic control of selected weeds in oilseed rape and in broadleaf, grass and perennial crops.

24 Claims, No Drawings

SYNERGISTIC HERBICIDAL COMPOSITIONS CONTAINING PROPYZAMIDE AND AMINOPYRALID

CROSS REFERENCE TO RELATED APPLICATIONS

This application claims the benefit of U.S. Provisional Patent Application Ser. No. 61/355,167 filed Jun. 16, 2010.

FIELD OF THE INVENTION

This invention concerns a synergistic herbicidal composition containing (a) propyzamide and (b) aminopyralid.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the Herbicide Handbook of the Weed Science Society of America, Ninth Edition, 2007, p. 429, "'synergism' [is] an interaction of two or more factors such that the effect when combined is greater than the predicted effect based on the response to each factor applied separately." The present invention is based on the discovery that (a) propyzamide and (b) aminopyralid, already known individually for their herbicidal efficacy, display a synergistic effect when applied in combination.

Propyzamide, 3,5-dichloro-N-(1,1-dimethylpropynyl) benzamide, is an amide herbicide. It is described in The Pesticide Manual, Fourteenth Edition, 2006. Propyzamide is applied either pre-emergence or early post-emergence to provide selective control of many annual and perennial grasses and some broadleaf weeds in a variety of crops.

Aminopyralid, 4-amino-3,6-dichloro-2-pyridinecarboxylic acid, is a picolinic acid or pyridine herbicide. It is described in The Pesticide Manual, Fourteenth Edition, 2006. Aminopyralid is used for long-term control of annual and perennial broadleaf weeds in grassland, pastures, some crops and industrial vegetation management.

SUMMARY OF THE INVENTION

The present invention concerns a synergistic herbicidal mixture comprising an herbicidally effective amount of (a) propyzamide and (b) aminopyralid. The compositions may also contain an agriculturally acceptable adjuvant or carrier.

The present invention also concerns a method of controlling the growth of undesirable vegetation, particularly in oilseed rape, but also in other broadleaf, grass and perennial crops, and the use of this synergistic composition.

The species spectrum of the compounds of the synergistic mixture, i.e., the weed species which the respective compounds control, is broad and highly complementary. These synergistic mixtures are particularly useful for the control of key weeds, e.g., wild chamomile (*Matricaria recutita* L; MATCH), chamomile species (*Matricaria* spp., MATSS), corn poppy (*Papaver rhoeas* L; PAPRH), blackgrass (*Alopecurus myosuroides* Huds.; ALOMY), annual bluegrass (*Poa annua* L.; POANN), and field violet (*Viola arvensis* Murr.; VIOAR), at application rates lower than the rates of the individual compounds.

It has also unexpectedly been found that the synergistic mixture exhibits a protecting effect against the phytotoxicity of aminopyralid on winter oilseed rape (*Brassica napus* L. ssp. napus; BRSNW).

DETAILED DESCRIPTION OF THE INVENTION

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the synergistic mixture when they are applied to the seed or locus of the plant before planting or emergence. The effect observed depends upon the plant species to be controlled, the application parameters of dilution, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention pre-emergence, prior to the emergence of the weeds with or without mechanical soil incorporation, or postemergence prior to, or after, emergence of weeds, to achieve the maximum control of weeds.

In the composition of this invention, the weight ratio of propyzamide (active ingredient) to aminopyralid (acid equivalent) at which the herbicidal effect is synergistic lies within the range of between about 14:1 and about 1120:1. Preferably the weight ratio of propyzamide to aminopyralid lies within the range of between about 56:1 and about 224:1.

The rate at which the synergistic composition is applied will depend upon the soil type, the particular type of weed to be controlled, the degree of control required, the length of weed control and the timing and method of application. In general, the composition of the invention can be applied at an application rate of between about 0.3 kilograms per hectare (kg/ha) and about 2.26 kg/ha based on the total amount of active ingredients in the composition. An application rate between about 0.4 kg/ha and about 1.7 kg/ha is preferred. In especially preferred embodiments of the invention, propyzamide (active ingredient) is applied at a rate between about 0.5 kg/ha and about 1.2 kg/ha and aminopyralid (acid equivalent) is applied at a rate between about 0.002 kg/ha and about 0.020 kg/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: asulam, benazolin, butachlor, butafenacil, butroxydim, carbetamide, clethodim, clomazone, clopyralid, cyanazine, cycloxydim, diclofop-methyl, diflufenzopyr, dimefuron, dimethachlor, dimethenamid, diquat, ethalfluralin, EPTC, fenoxaprop-p-ethyl, fluazifop, fluazifop-P-butyl, glufosinate, glufosinate-ammonium, glyphosate, haloxyfop-methyl, haloxyfop-R, imazamethabenz, imazamox, imazapic, imazapyr, imazaquin, imazethapyr, imazosulfuron, metazachlor, napropamide, propaquizafop, quinmerac, quizalofop-P-butyl, quizalofop-P-ethyl, quizalofop-p-tefuryl, sethoxydim, simazine, sulfosate, tepraloxidim and trifluralin.

The compounds of the present invention can additionally be employed to control undesirable vegetation in many crops that have been made tolerant to or resistant to them or to other herbicides by genetic manipulation or by mutation and selection. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix. Similarly the herbicidal compounds of the present invention can be used in conjunction with acetolactate synthase inhibitors on acetolactate synthase inhibitor-tolerant crops.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

While it is possible to utilize the synergistic mixture of the present invention directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of the synergistic mixture or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The compositions may also contain other compatible components, for example, other herbicides, plant growth regulators, fungicides, insecticides, and the like, and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 10 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.1 to 20 weight percent active ingredient and preferably contain 0.4 to 7.0 weight percent.

The present compositions can be applied to weeds or their locus by the use of conventional ground or aerial dusters, sprayers, and granule applicators and by other conventional means known to those skilled in the art.

and in combination, to measure herbicidal weed control and any synergistic interactions. Treatments were rated at different intervals from treatment to time of evaluation up to the following year when the crop starts to grow again in the spring. The weed efficacy was compared to the untreated control plants. Visual weed control was scored on a scale of 0 to 100 percent where 0 corresponds to no injury and 100 corresponds to complete kill.

Colby's equation was used to determine the herbicidal effects expected from the mixtures (Colby, S. R. *Weeds* 1967, 15, 20-22. Calculation of the synergistic and antagonistic response of herbicide combinations.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture;

B=observed efficacy of active ingredient B at the same concentration as used in the mixture.

The herbicide tank mix combinations tested, application rates and ratios employed, plant species tested, and results are given in Tables 1 to 4.

TABLE 1

Synergistic Herbicidal Activity from Pre-emergence Applications on Residual Weed Control in the Field when rated 112 to 188 Days after Application.

| Application Rate | | % Control | | | | | | |
|---|---|---|---|---|---|---|---|---|
| Propyzamide | Aminopyralid | MATCH | | PAPRH (1) | | PAPRH (2) | | VIOAR | |
| (g ai/ha) | (g ae/ha) | Ob | Ex | Ob | Ex | Ob | Ex | Ob | Ex |
| 750 | 0 | 0 | — | 18 | — | 0 | — | 27 | — |
| 0 | 6 | 80 | — | 48 | — | 0 | — | 0 | — |
| 750 | 6 | 93 | 80 | 68 | 57 | 100 | 0 | 68 | 27 |
| 750 | 0 | — | — | 18 | — | 0 | — | 27 | — |
| 0 | 8 | — | — | 68 | — | 75 | — | 0 | — |
| 750 | 8 | — | — | 90 | 74 | 100 | 75 | 68 | 27 |

MATCH = *Matricaria recutita* L. (wild chamomile)
PAPRH = *Papaver rhoeas* L. (corn poppy)
VIOAR = *Viola arvensis* Murr. (field violet)
Ob = Observed visual weed control
Ex = Expected weed control as defined by Colby Equation
PAPRH (1) = France
PAPRH (2) = Great Britain
g ai/ha = grams of active ingredient per hectare
g ae/ha = grams of acid equivalent per hectare

EXAMPLES

Evaluation of Propyzamide+Aminopyralid Tank Mixes for Synergistic Weed Control in Oilseed Rape Field trials were conducted in winter oilseed rape crop using small plot research methodology. The oilseed rape crop was grown using normal cultural practices for the respective area of the trials, using varieties, fertilization and maintenance to ensure normal growth of the crop and the weeds. Plot size was 2 meters (m) wide by 10 m long with 4 replicates by treatment. All treatments were applied preemergence to early postemergence to the weeds using a compressed air backpack sprayer delivering 200 liters per hectare (L/ha) spray volume. Commercially available product of propyzamide/pronamide was mixed with a formulation of aminopyralid potassium at appropriately formulated product rates to achieve the desired rates based on a unit area of application (hectare) to achieve the desired rates as shown. Treatments consisted of propyzamide applied alone, as well as aminopyralid applied alone,

TABLE 2

Synergistic Herbicidal Activity from Pre-emergence Applications on Residual Weed Control in the Field when rated 93 to 188 Days after Application.

| Application Rate | | % Control | | | |
|---|---|---|---|---|---|
| Propyzamide | Aminopyralid | PAPRH (2) | | MATSS | |
| (g ai/ha) | (g ae/ha) | Ob | Ex | Ob | Ex |
| 840 | 0 | 11 | — | — | — |
| 0 | 6 | 48 | — | — | — |
| 840 | 6 | 73 | 54 | — | — |
| 840 | 0 | 11 | — | — | — |
| 0 | 8 | 68 | — | — | — |
| 840 | 8 | 89 | 72 | — | — |
| 750 | 0 | — | — | 7 | — |

TABLE 2-continued

Synergistic Herbicidal Activity from Pre-emergence Applications on Residual Weed Control in the Field when rated 93 to 188 Days after Application.

| Application Rate | | % Control | | | |
|---|---|---|---|---|---|
| Propyzamide | Aminopyralid | PAPRH (2) | | MATSS | |
| (g ai/ha) | (g ae/ha) | Ob | Ex | Ob | Ex |
| 0 | 10 | — | — | 48 | — |
| 750 | 10 | — | — | 72 | 52 |

PAPRH = *Papaver rhoeas* L. (corn poppy)
MATSS = *Matricaria* spp L. (chamomile species)
Ob = Observed visual weed control
Ex = Expected weed control as defined by Colby Equation
PAPRH (2) = Great Britain
g ai/ha = grams of active ingredient per hectare
g ae/ha = grams of acid equivalent per hectare

TABLE 3

Synergistic Herbicidal Activity from Pre-emergence Applications on Residual Weed Control in the Field when rated 93 to 200 Days after Application.

| Application Rate | | % Control | | | | | |
|---|---|---|---|---|---|---|---|
| Propyzamide | Aminopyralid | ALOMY | | POANN (1) | | POANN (2) | |
| (g ai/ha) | (g ae/ha) | Ob | Ex | Ob | Ex | Ob | Ex |
| 750 | 0 | 75 | — | 22 | — | 22 | — |
| 0 | 6 | 0 | — | 0 | — | 0 | — |
| 750 | 6 | 100 | 75 | 47 | 22 | 47 | 22 |
| 750 | 0 | 75 | — | 22 | — | 22 | — |
| 0 | 8 | 0 | — | 0 | — | 0 | — |
| 750 | 8 | 97 | 75 | 47 | 22 | 47 | 22 |
| 840 | 0 | — | — | 22 | — | — | — |
| 0 | 6 | — | — | 0 | — | — | — |
| 840 | 6 | — | — | 50 | 22 | — | — |
| 840 | 0 | — | — | 22 | — | — | — |
| 0 | 8 | — | — | 0 | — | — | — |
| 840 | 8 | — | — | 43 | 22 | — | — |

ALOMY = *Alopecurus myosuroides* Huds. (blackgrass)
POANN = *Poa annua* L. (annual bluegrass)
Ob = Observed visual weed control
Ex = Expected weed control as defined by Colby Equation
POANN (1) = Great Britain
POANN (2) = Great Britain
g ai/ha = grams of active ingredient per hectare
g ae/ha = grams of acid equivalent per hectare

TABLE 4

Synergistic Herbicidal Activity from Pre-emergence Applications on Crop Tolerance in the Field when rated 167 Days after Application.

| Application Rate | | % Crop Injury | |
|---|---|---|---|
| Propyzamide | Aminopyralid | BRSNW | |
| (g ai/ha) | (g ae/ha) | Ob | Ex |
| 750 | 0 | 0 | — |
| 0 | 6 | 23 | — |
| 750 | 6 | 8 | 23 |
| 750 | 0 | 0 | — |
| 0 | 8 | 22 | — |
| 750 | 8 | 2 | 22 |
| 840 | 0 | 2 | — |
| 0 | 6 | 23 | — |

TABLE 4-continued

Synergistic Herbicidal Activity from Pre-emergence Applications on Crop Tolerance in the Field when rated 167 Days after Application.

| Application Rate | | % Crop Injury | |
|---|---|---|---|
| Propyzamide | Aminopyralid | BRSNW | |
| (g ai/ha) | (g ae/ha) | Ob | Ex |
| 840 | 6 | 5 | 24.5 |
| 840 | 0 | 2 | — |
| 0 | 8 | 22 | — |
| 840 | 8 | 8 | 23.6 |

BRSNW = *Brassica napus* L. ssp. *Napus* (winter oil seed rape)
Ob = Observed visual weed control
Ex = Expected weed control as defined by Colby Equation
g ai/ha = grams of active ingredient per hectare
g ae/ha = grams of acid equivalent per hectare

What is claimed is:

1. A synergistic herbicidal mixture comprising an herbicidally effective amount of (a) propyzamide and (b) aminopyralid, wherein the ratio of propyzamide active ingredient weight to aminopyralid acid equivalent weight is from about 56:1 to about 224:1.

2. An herbicidal composition comprising an herbicidally effective amount of the synergistic herbicidal mixture of claim 1 and an agriculturally acceptable adjuvant or carrier.

3. A method of controlling undesirable vegetation which comprises contacting the seed, or locus of the crop before planting or emergence, or applying to the soil to control the growth and/or emergence of the undesirable vegetation, or applying to weeds prior to or after emergence of weeds, an herbicidally effective amount of the synergistic herbicidal mixture of claim 1.

4. A method of controlling undesirable vegetation in oilseed rape, which comprises contacting the seed, or locus of the oilseed rape plant before planting or emergence, or applying to the soil to control the growth and/or emergence of the undesirable vegetation, or applying to weeds prior to or after emergence of weeds, an herbicidally effective amount of the synergistic herbicidal mixture of claim 1.

5. A method of protecting winter oilseed rape against the phytotoxicity of aminopyralid which comprises safening the phytotoxicity of aminopyralid with propyzamide, wherein the ratio of propyzamide active ingredient weight to aminopyralid acid equivalent weight is from about 93:75:1 to about 140:1.

6. The synergistic mixture of claim 1 in which the ratio of propyzamide active ingredient weight to aminopyralid acid equivalent weight is between about 75:1 and about 125:1.

7. The method of claim 3, wherein the undesirable vegetation is *Matricaria*, *Papaver*, *Alopecurus*, *Poa*, or *Viola*.

8. The method of claim 3, wherein the undesirable vegetation is *Matricaria recutita* L., *Matricaria* spp. L, *Papaver rhoeas* L., *Alopecurus myosuroides* Huds., *Poa annua* L., or *Viola arvensis* Murr.

9. The method of claim 4, wherein the undesirable vegetation is *Matricaria*, *Papaver*, *Alopecurus*, *Poa*, or *Viola*.

10. The method of claim 4, wherein the undesirable vegetation is *Matricaria recutita* L., *Matricaria* spp. L, *Papaver rhoeas* L., *Alopecurus myosuroides* Huds., *Poa annua* L., or *Viola arvensis* Murr.

11. A method for controlling undesirable vegetation comprising contacting soil or the undesirable vegetation with a herbicidally effective amount of (a) propyzamide and (b)

aminopyralid, wherein the ratio of propyzamide active ingredient weight to aminopyralid acid equivalent weight is from about 56:1 to about 224:1.

12. The method of claim 11, wherein the soil or undesirable vegetation is contacted with a composition comprising aminopyralid and propyzamide.

13. The method of claim 11, wherein the method is performed in the presence of a crop or crop seed.

14. The method of claim 13, wherein the crop or crop seed is an oilseed rape crop or crop seed.

15. The method of claim 13, wherein contacting is performed prior to emergence of the crop.

16. The method of claim 13, wherein the contacting is performed after emergence of the crop.

17. The method of claim 13, wherein the contacting is performed prior to emergence of the undesirable vegetation.

18. The method of claim 13, wherein the contacting is performed after the emergence of the undesirable vegetation.

19. The method of claim 11, wherein the weight ratio is from about 75:1 to about 140:1.

20. The method of claim 11, wherein the undesirable vegetation is *Matricaria, Papaver, Alopecurus, Poa*, or *Viola*.

21. The method of claim 20, wherein the undesirable vegetation is *Matricaria recutita* L., *Matricaria* spp. L, *Papaver rhoeas* L., *Alopecurus myosuroides* Huds., *Poa annua* L., or *Viola arvensis* Murr.

22. The method of claim 13, wherein (a) the crop is glyphosate-tolerant and undesirable vegetation is further contacted with glyphosate; (b) the crop is glufosinate-tolerant and the undesirable vegetation is further contacted with glufosinate; (c) the crop is dicamba-tolerant and the undesirable vegetation is further contacted with dicamba; or (d) the crop is imidazolinone-tolerant and the undesirable vegetation is further contacted with an imidazolinone.

23. The mixture of claim 11, wherein the ratio from about 75:1 to about 125:1.

24. The mixture of claim 11, wherein the ratio is about 93:75:1.

* * * * *